US00PP16458P2

(12) United States Plant Patent
Crippen

(10) Patent No.: US PP16,458 P2
(45) Date of Patent: Apr. 18, 2006

(54) ***CLERODENDRUM* PLANT NAMED 'MORNINGSTAR'**

(50) Latin Name: *Clerodendrum quadriloculare*
Varietal Denomination: Morningstar

(75) Inventor: Joel Crippen, West Palm Beach, FL (US)

(73) Assignee: Morningstar Nursery, Inc., West Palm Beach, FL (US)

( * ) Notice: Subject to any disclaimer, the term of this patent is extended or adjusted under 35 U.S.C. 154(b) by 89 days.

(21) Appl. No.: 10/949,931

(22) Filed: Sep. 24, 2004

(51) Int. Cl.
*A01H 5/00* (2006.01)

(52) U.S. Cl. ..... Plt./226
(58) Field of Classification Search ..... Plt./226
See application file for complete search history.

*Primary Examiner*—Anne Marie Grunberg
(74) *Attorney, Agent, or Firm*—C. A. Whealy

(57) ABSTRACT

A new and distinct cultivar of *Clerodendrum* plant named 'Morningstar', characterized by its compact, upright and outwardly spreading plant growth habit; dark green and lighter green variegated leaves; relatively small ruffled leaves; freely flowering habit; and purple and white-colored flowers.

3 Drawing Sheets

Botanical classification/cultivar designation: *Clerodendrum quadriloculare* cultivar Morningstar.

BACKGROUND OF THE INVENTION

The present Invention relates to a new and distinct cultivar of *Clerodendrum* plant, botanically known as *Clerodendrum quadriloculare,* and hereinafter referred to by the name 'Morningstar'.

The new *Clerodendrum* is a naturally-occurring branch mutation of an unnamed selection of *Clerodendrum quadriloculare*, not patented. The new *Clerodendrum* was discovered by the Inventor in a controlled environment in Delray Beach, Fla., within a population of plants of the unidentified selection in the spring of 2001. The new *Clerodendrum* was selected on the basis of its compact plant habit and ruffled leaves.

Asexual reproduction of the new cultivar by vegetative cuttings in a controlled environment in Delray Beach, Fla. since 2001, has shown that the unique features of this new *Clerodendrum* are stable and reproduced true to type in successive generations.

SUMMARY OF THE INVENTION

Plants of the cultivar Morningstar have not been observed under all possible environmental conditions. The phenotype may vary somewhat with variations in environment such as temperature and light intensity without, however, any variance in genotype.

The following traits have been repeatedly observed and are determined to be the unique characteristics of 'Morningstar'. These characteristics in combination distinguish 'Morningstar' as a new and distinct cultivar:

1. Compact, upright and outwardly spreading plant growth habit.
2. Dark green and lighter green variegated leaves.
3. Relatively small ruffled leaves.
4. Freely flowering habit.
5. Purple and white-colored flowers.

Plants of the new *Clerodendrum* are most similar to plants of the parent selection. In side-by-side comparisons conducted in Delray Beach, Fla., plants of the new *Clerodendrum* differed from plants of the parent selection in the following characteristics:

1. Plants of the new *Clerodendrum* were more compact and less vigorous than plants of the parent selection.
2. Plants of the new *Clerodendrum* had variegated leaves whereas plants of the parent selection had solid green-colored leaves.
3. Plants of the new *Clerodendron* had ruffled leaves whereas plants of the parent selection had flat leaves.
4. Plants of the new *Clerodendrum* were more freely flowering than plants of the parent selection.

Plants of the new *Clerodendrum* can be compared to plants of the *Clerodendrum* cultivar Brandonii, disclosed in U.S. Plant Pat. No. 12,140. Plants of the new *Clerodendrum* are more compact than plants of the cultivar Brandonii. In addition, plants of the new *Clerodendron* and the cultivar Brandonii differ in leaf variegation.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the colors of the new *Clerodendrum.*

The photograph on the first sheet comprises a side perspective view of typical plants of 'Morningstar' (left) and the parent selection (right).

The photograph on the second sheet is a close-up view of typical flowers of 'Morningstar'.

The photograph on the third sheet is a close-up view of typical leaves of 'Morningstar'.

DETAILED BOTANICAL DESCRIPTION

In the following description, color references are made to The Royal Horticultural Society Colour Chart, 1995 Edition, except where general terms of ordinary dictionary significance are used. Plants used in the aforementioned photographs and for the following description were grown in 25-cm containers for about two years in a polypropylene-covered shadehouse and under condition which closely approximate commercial production conditions in Delray Beach, Fla. During the production of the plants, day temperatures ranged from 23 to 29° C. and night temperatures ranged from 12 to 18° C. Plants were pinched in the late summer and the photographs and description were taken during the following late winter and early spring.

Botanical classification: *Clerodendrum quadriloculare* cultivar Morningstar.

Parentage: Naturally-occurring branch mutation of an unnamed selection of *Clerodendrum quadriloculare*, not patented.

Propagation:

*Type*.—Vegetative cuttings.

*Time to produce a rooted cutting*.—About five to six weeks.

*Root description*.—Fibrous; tan, 159C, in color.

Plant description:

*Form*.—Perennial subshrub; compact, upright and outwardly spreading plant growth habit; rounded plant form. New leaves marked with variable areas of pale green, angular variegation. Mature leaves dark green with variable areas of lighter green variegation. Leaves become twisted and undulate with maturity, giving the foliage a dense ruffled appearance.

*Plant height*.—About 75 cm; at maturity, about 2 meters.

*Plant diameter*.—About 80 cm; at maturity, about 2 meters.

*Vigor*.—Moderately vigorous.

*Stem description*.—Shape. Quadrangular. Diameter: About 7 cm. Internode length: About 7 to 12 cm. Branching habit: Opposite; freely branching. Color: Young stems, darker than, but closest to 187A with occasional streaks of 187B and small raised areas of 199C. Mature stems, 199C, with areas of 147A. Leaf scars, 199B, often tinged with 147B.

*Foliage description*.—Appearance: Undulate and often twisted. Dark green in color with variably marked lighter green variegation. Variegation most apparent on immature and newly expanded leaves, becoming somewhat less distinct as leaves mature. Arrangement: Opposite, simple. Length: Larges: leaves, about 17 to 21 cm; average size leaves, about 11 to 15 cm. Width: Largest leaves, about 7 to 8 cm; average size leaves, about 6 to 7 cm. Thickness: About 0.8 mm. Aspect: Petiole tilted about 30 to 45° from vertical. Leaves arch outwardly. Leaves variably curved and twisted, ruffled in appearance. Leaf apex often curled or curved downward. Shape: Ovate to somewhat lanceolate. Apex: Acute to acuminate. Base: Attenuate. Margin: Entire; undulate. Texture, upper and lower surfaces: Glabrous; rugose. Venation pattern: Pinnate. Color: Developing foliage, upper surface: Much darker than but closest to 147A; areas of variegation, 147B; midrib, 147A, tinged with 187A; primary veins, 147A. Developing foliage, lower surface: 187A; midrib, 187A; primary veins, 187A. Fully expanded foliage, upper surface: Darker than but closest to 147A; areas of variegation, 147A to 147B; midrib, 187A to 187A, tinged with 147A; primary veins, 147A. Fully expanded foliage, lower surface: 187A; midrib, 187A; primary veins, 187A. Petiole: Length: About 4 to 6.5 cm. Diameter: About 4 mm. Texture, upper and lower surfaces: Glabrous. Color, upper and lower surfaces: 187A to 187B.

Flower description:

*Flower type and habit*.—Flowers single, gamopetalous, salverform; limb with four reflexed lobes. Flowers arranged on compound terminal cymes; cymes globose in shape. Flowers face upright and outwardly. Flowers not persistent.

*Natural flowering season*.—Flowering continuous from January to March in Delray Beach, Fla.

*Quantity*.—Freely flowering with about 40 to 75 flowers per inflorescence.

*Fragrance*.—None detected.

*Flower longevity on the plant*.—Individual flowers remain open for about three days before fading. Inflorescences continue to flower for about four weeks.

*Inflorescence diameter*.—About 15 to 20 cm.

*Flower bud color*.—Tube, 78A to 78B; reverse of limb, 78A with 155D.

*Flower diameter*.—About 2 cm.

*Lobe diameter*.—About 5 mm.

*Tube length*.—About 9.9 cm.

*Tube diameter*.—About 2 mm.

*Limb color, upper surface*.—155D.

*Limb color, lower surface*.—155D; towards the apex, 78A to 78B; streaks, 78A to 78B.

*Sepals*.—Quantity/arrangement: Five sepals fused at base; inconspicuous. Length: About 4 mm. Diameter: About 1.5 mm. Shape: Triangular. Apex: Acute. Margin: Entire. Texture, upper and lower surfaces: Glabrous. Color, upper and lower surfaces: 187A tinged with 147A.

*Reproductive structures*.—Androecium: Quantity: Four stamens per flower. Filament length: About 1.8 cm. Filament diameter: About 0.5 mm. Filament color: 155D. Anther length: About 3 mm. Anther diameter: About 1 mm. Anther color: 200A. Pollen color: 10D. Gynoecium: Quantity: One per flower. Style length: About 11.4 cm. Style diameter: About 0.4 mm. Style color: 155A. Stigma shape: Bifurcate; reflexed. Stigma size: Each lobe about 1 mm in length, about 0.5 mm in diameter. Stigma color: 183C. Ovary diameter: About 2 mm. Ovary color: 146A.

*Seeds/fruits*.—Seed and fruit development has not been observed.

Disease/pest resistance: Resistance to pathogens or pests common to *Clerodendrum* has not been observed.

Temperature tolerance: Plants of the new *Clerodendrum* have been observed to be tolerant to temperatures from about −7 to 35° C.

It is claimed:

1. A new and distinct cultivar of *Clerodendrum* plant named 'Morningstar', as illustrated and described.

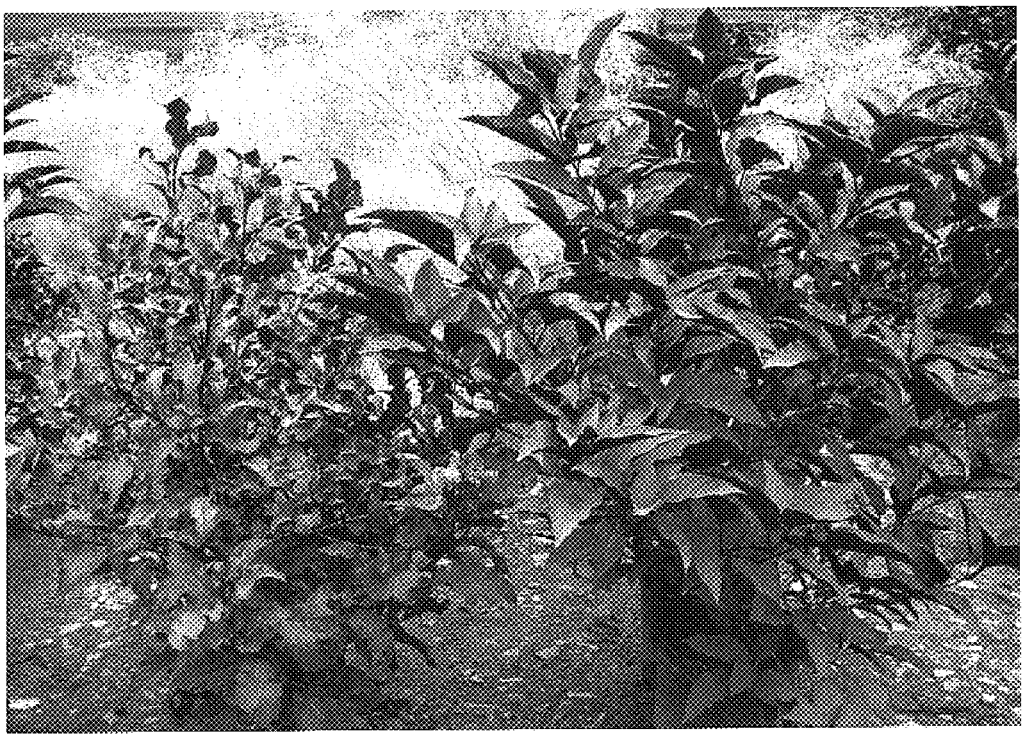

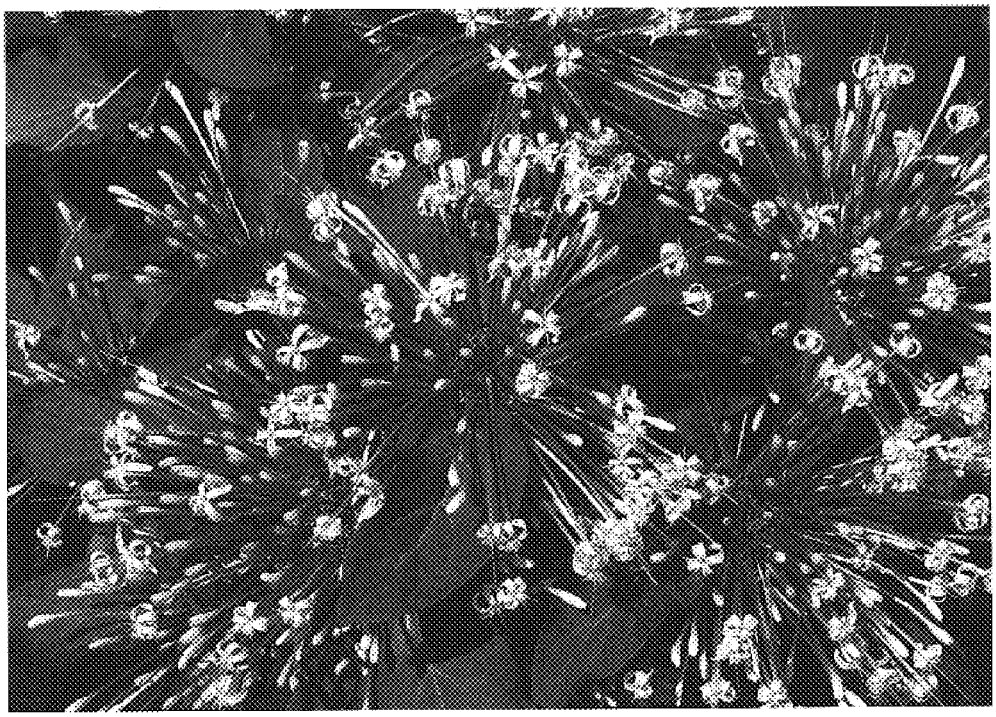

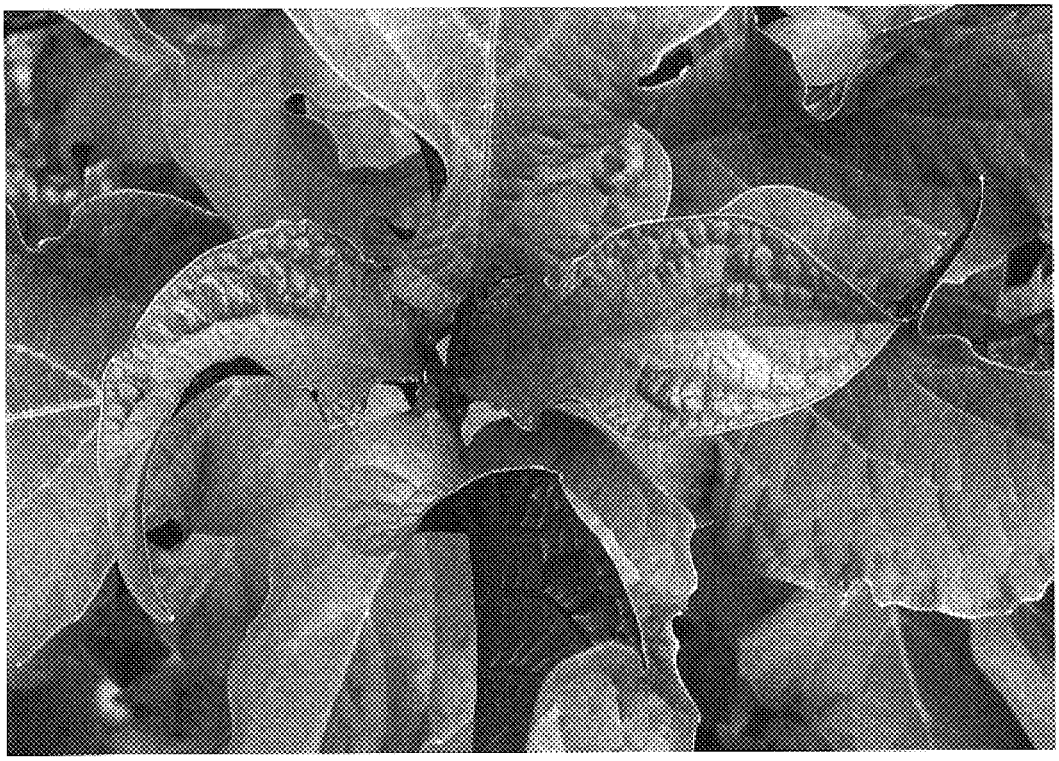

* * * * *